United States Patent [19]

Woo et al.

[11] Patent Number: 4,642,351

[45] Date of Patent: Feb. 10, 1987

[54] PREPARATION OF N-SUBSTITUTED IMIDAZOLIDINONES AND N-SUBSTITUTED 2-THIONIMIDAZOLIDINONES

[75] Inventors: Edmund P. Woo; Diana R. Price, both of Midland, Mich.

[73] Assignee: The Dow Chemical Company, Midland, Mich.

[21] Appl. No.: 459,432

[22] Filed: Jan. 20, 1983

[51] Int. Cl.$^4$ ............................................ C07D 233/36
[52] U.S. Cl. .................................. 548/317; 548/320; 548/321; 548/322
[58] Field of Search ................ 548/317, 320, 321, 322

[56] References Cited

U.S. PATENT DOCUMENTS 3,119,833  1/1964  Sovish ................................ 548/231
3,876,657  4/1975  Aelony et al. .................. 424/273 R

FOREIGN PATENT DOCUMENTS 1065295  4/1967  United Kingdom ................ 548/317

OTHER PUBLICATIONS

Dyen, M., et al., *Chem. Rev.*, 67, pp. 197 and 226 (1967).
Baltzly, R., et al., *J. Am. Chem. Soc.*, 62, 164 (1940).
Bergmann, E., et al., *J. Org. Chem.*, 16, 84 (1951).
Ide, W., et al., *J. Am. Chem. Soc.*, 70, 1084 (1984).
English Translation of Krieg, B. et al., *Liebigs Ann. Chem.*, 1976, 208-221.
Yates, P., et al., *J. Am. Chem. Soc.*, 82, 4436 (1960).
Wright, W., et al., *J. Med. Chem.*, 9(6), 852 (1966).
Najer, H., et al., *Bull. Soc. Chim. France*, 323 (1963).
Gulbins, E., *Liebigs Ann. Chem.*, 1966, 698, 180-185.
Aelony, D., et al., *J. Heterocycl. Chem.*, 1972, 9(3), 687-690.
March, J., *Advanced Organic Chemistry*, McGraw Hill, New York, 1968, p. 658.

*Primary Examiner*—Richard A. Schwartz
*Attorney, Agent, or Firm*—N. L. Sims

[57] ABSTRACT

The invention is a process for the preparation of N-substituted imidazolidinones and N-substituted 2-thionimidazolidinones which comprises contacting an oxazolidinone with a compound containing a nitrogen directly bonded to a carbonyl or a thiocarbonyl group in the presence of a Lewis acid catalyst or the hydrate of a Lewis acid catalyst under conditions such that an N-substituted imidazolidinone or N-substituted 2-thionimidazolidinone is prepared. The compound containing a nitrogen directly bonded to a carbonyl or a thiocarbonyl group is an isocyanate or isothiocyanate or a compound wherein the nitrogen is reactive and the carbonyl or thiocarbonyl group is further bonded to a substituent by a bond which is clevable under the reaction conditions. The Lewis acid catalyst corresponds to the formula $$MX_n$$

wherein
M is a group IB-VIIIB, IIIA or IVA element with the proviso that M is not C or Si;
X is a halogen; and
n is 2, 3 or 4.

16 Claims, No Drawings

PREPARATION OF N-SUBSTITUTED IMIDAZOLIDINONES AND N-SUBSTITUTED 2-THIONIMIDAZOLIDINONES

BACKGROUND OF THE INVENTION

This invention relates to a novel process for the preparation of N-substituted imidazolidinones and N-substituted 2-thionimidazolidinones.

N-substituted imidazolidinones and N-substituted 2-thionimidazolidinones have recognized utility as bactericides, central nervous system depressants, plant growth promoters, female fly sterilants, adhesives, textile treating agents, and as monomers for deriving polymers and copolymers.

N-substituted imiadazolidinones can be prepared by several prior art processes. Wright et al., *J. Med. Chem.*, 9, 856 (1966), teach a three-step process for such preparation wherein an aniline, which can be substituted, is reacted with 2-bromoethylamine in the presence of base, such as potassium hydroxide, to prepare an N-phenylethylenediamine. The product is thereafter reacted with potassium cyanate to prepare a 2-anilinoethyl urea, which is thereafter thermolytically cyclized to form the N-substituted imidazolidinone by heating the anilinoethyl urea in an oil bath at about 220° C. This process has significant disadvantages including the use of toxic bromoethylamine, two of the steps produce a salt and the synthesis described requires three steps.

Najer et al., *Bull. Soc. Chem. France*, 323–8 (1963), teach that N-substituted imidazolidinones may be prepared by the reaction of aziridine with an organic isocyanate to prepare a urea intermediate represented by the formula

The urea intermediate is thereafter contacted with sixfold molar excess of sodium iodide in dimethyl carbonate and refluxed for 30 hours to prepare N-substituted imidazolidinones. This process has several disadvantages including the use of highly toxic aziridine as a starting material, the requirement of large amounts of sodium iodide in the second step and long reaction times.

Gulbins et al., *Justus Liebigs Ann. Chem.*, 698, 180 (1966), teach that N-substituted aziridines can be reacted with isocyanates in the presence of lithium chloride or lithium bromide catalysts at elevated temperatures to prepare N-substituted imidazolidinones. A major competing reaction is the trimerization of the isocyanates. The major disadvantages of this process are the use of highly toxic aziridine as a starting material and the comprising trimerization of the isocyanates.

Aelony et al., U.S. Pat. No. 3,876,657; see also *J. Heterocyclic Chem.*, 9, 687 (1972); disclose a three-step process for the preparation of N-substituted imidazolidinones. In the first step an amine is reacted with an acrylic ester to form an adduct. In the second step, the adduct is converted to an aminimide by the reaction of the adduct with a trialkyl hydrazinium halide in the presence of a suitable dehydrohalogenating agent or by reaction of the adduct with an asymmetrical disubstituted hydrazine and a lower alkylene oxide. The tertiary amine monoimides are thermolytically rearranged to prepare the imidazolidinones by heating them at a temperature in excess of 140° C. for a sufficient time. The use of strong bases in the synthesis and the multistep synthesis required are two major disadvantages with this process.

In British Pat. No. 1,065,295, N-substituted imidazolidinones prepared by reacting oxazolidinones with an isocyanate at an elevated temperature and preferably in the presence of a catalyst which is a tertiary amino base or lithium chloride. It is further disclosed that preferred temperatures are between about 120° C. and 180° C. with a reaction time of 4 to 12 hours. The catalysts can be used in amounts such as 1/20 mole per mole of the initial oxazolidinone. The examples demonstrate the use of catalyst amounts varying between about 10 and 33 mole percent based on the moles of oxazolidinone. The major disadvantage of this process is the requirement of a relatively large amount of catalyst.

Unfortunately each of the prior art processes described has one or more disadvantages. The most prevalent is the requirement of large amounts of base to catalyze the reaction. Other major disadvantages are that some of the processes use toxic reactants, some require multistep reaction sequences, and some processes produce salt by-products. Long reaction times are another major disadvantage.

A process which is simple, which does not use base and uses small amounts of catalyst for the reaction is desirable. A process which does not use toxic reactants or produce salt by-products is also desirable.

SUMMARY OF THE INVENTION

The invention is a process for the preparation of N-substituted imidazolidinones and N-substituted 2-thionimidazolidinones which comprises contacting an oxazolidinone with a compound containing a nitrogen directly bonded to a carbonyl or a thiocarbonyl group in the presence of a Lewis acid catalyst or the hydrate of a Lewis acid catalyst under conditions such that an N-substituted imidazolidinone or N-substituted 2-thionimidazolidinone is prepared. The compound containing a nitrogen directly bonded to a carbonyl or a thiocarbonyl group is an isocyanate or isothiocyanate or a compound wherein the nitrogen is reactive and the carbonyl or thiocarbonyl group is further bonded to a substituent by a bond which is cleavable under the reaction conditions. The Lewis acid catalyst corresponds to the formula

wherein
M is a group IB–VIIIB, IIIA or IVA element with the proviso that M is not C or Si;
X is a halogen; and
n is 2, 3 or 4.

Surprisingly, the Lewis acids described above are very good catalysts for the preparation of imidazolidinones. Further, surprisingly smaller amounts of the Lewis acid catalysts than the prior art basic or alkaline halide catalysts are required to catalyze the reaction.

DETAILED DESCRIPTION OF THE INVENTION

Desirable compounds which contain a nitrogen directly bonded to a carbonyl group or a thiocarbonyl group (hereinafter referred to as a nitrogen carbonyl compound) include isocyanates or isothiocyanates which correspond to the formula, $$R^1N=C=Y$$

wherein Y is oxygen or sulfur. Also desirable are compounds wherein the nitrogen is reactive under the reaction conditions and the carbonyl or thiocarbonyl is further bonded by a cleavable bond under the reaction conditions to another substituent, such compounds include those corresponding to the formula,

In the above formulas $R^1$ is a $C_{1-20}$ hydrocarbyl radical optionally substituted with a halogen, aryloxy, alkoxy, nitro, thioaryloxy, or thioalkoxy group;

$R^2$ is halogen, alkoxy, aryloxy, thioalkyl, thioaryl, mercapto, alkylsulfonamido, alkylsulfinyl, alkylsulfonoyl, alkylamino, arylamino, alkanoylamino or alkanoylimino; and Y is oxygen or sulfur.

$R^1$ is preferably a $C_{6-20}$ aromatic or $C_{6-10}$ cycloaliphatic radical optionally substituted with a $C_{1-10}$ alkyl, a $C_{6-10}$ aryl, halogen, nitro, aryloxy, or alkoxy group. More preferably $R^1$ is a phenyl group optionally substituted with a halogen, $C_{1-10}$ alkyl, nitro, aryloxy or alkoxy, and most preferably a phenyl group optionally substituted with a methyl, nitro or chloro group. $R^2$ is preferably a halogen, alkylamino, aryloxy or alkyloxy, and most preferably aryloxy or alkoxy. Y is preferably oxygen.

Reactive nitrogen means that the hydrogen atom attached to the nitrogen readily leaves under the reaction conditions so that the nitrogen can further react with the oxazolidinone to form the bonds necessary to prepare the imidazolidinone or 2-thionimidazolidinone. It has been found that where R' is an aromatic group, the nitrogen is more reactive. Readily cleavable bond in reference to the carbonyl or thiocarbonyl group means herein that under the reaction conditions, the bond breaks leaving the carbonyl or thiocarbonyl group free to further react with the oxazolidinone or 2-thionoxazolidinone. Bonds between the carbon of the carbonyl or thiocarbonyl group and an oxygen, nitrogen, sulfur or halogen and the like are readily cleavable. The use of an isocyanate or isothiocyanate is preferred for this process as higher yields are generally achieved with them, and an isocyanate is most preferred.

Oxazolidinones preferred for use in this process include those represented by the formula

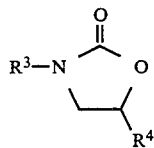

wherein $R^3$ is hydrogen, or a $C_{1-20}$ hydrocarbyl radical optionally substituted with a halogen aryloxy, alkyloxy, aryl, or nitro group; and $R^4$ is hydrogen or $R^3$.

$R^3$ is preferably a $C_{1-20}$ alkyl group optionally substituted with a halogen, and most preferably hydrogen or a $\beta$-chloroethyl group. $R^4$ is preferably hydrogen.

Preferred N-substituted imidazolidinones and N-substituted 2-thionimidazolidinones prepared by this process include those represented by the

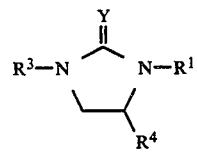

wherein $R^1$, $R^3$ and $R^4$ are as defined above.

The catalyst for this process is a Lewis acid corresponding to the formula $MX_n$ or hydrates of such Lewis acids. Preferably, M is aluminum, zinc, nickel or iron, and most preferably aluminum. X is preferably chlorine. Preferable catalysts include aluminum chloride, iron chloride, zinc chloride and nickel chloride. A most preferred catalyst is aluminum chloride.

The processes for preparing imidazolidinones and 2-thionimidazolidinones of this invention are described by the following equations. When an isocyanate or isothiocyanate is the nitrogen carbonyl compound, the process is described by equation I

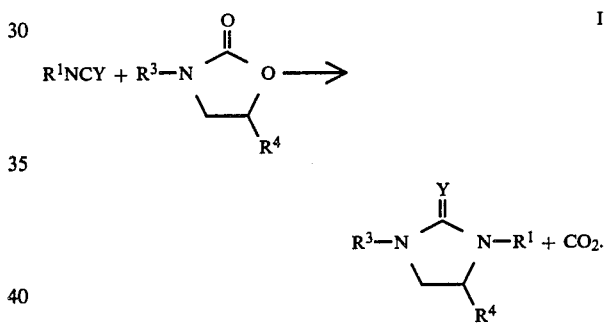

Where the nitrogen carbonyl compound is

the process is described by equation II

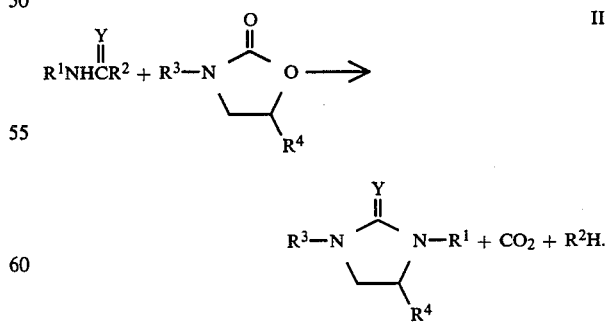

In the processes taught herein carbon dioxide is a by-product. Generally, cessation of carbon dioxide evolution indicates that the reaction is complete.

The nitrogen carbonyl compound is contacted with the oxazolidinone in molar ratios of between about 2:1 and 1:2, preferably about 1:1. There is no real advantage in using an excess of either reactant.

A wide range of molar amounts of catalyst can be used in this invention. The practical lower limit is that amount which gives a reasonable reaction rate, as even traces of the catalyst catalyze the reaction. The practical upper limit is dictated by economy. If too much catalyst is used, then residual catalyst may be retained in the product unless costly removal steps are instituted. The catalyst is preferably used in amounts between about 0.01 and 5.0 mole percent based upon the oxazolidinone, and most preferably between about 0.1 and 2.0 mole percent.

The reactants are usually contacted neat, that is in the absence of a solvent. A solvent may be used, but no advantage is gained through the use of a solvent. Suitable solvents are inert to the reactants and include chlorobenzenes, nitrobenzenes, diphenylsulfone and the like.

Elevated temperatures are necessary in this process. Temperatures are preferably between about 150° C. and 220° C., and most preferably between 180° C. and 200° C. Below 150° C. the reaction rate is extremely slow.

The reactions described herein usually take between 2 and 24 hours to complete.

SPECIFIC EMBODIMENTS

The following examples are included for illustrative purposes and do not limit the scope of the invention or claims.

EXAMPLE 1

Preparation of N-(3-chlorophenyl)-N'-(2-chloroethyl)imidazolidinone

A mixture of 3-chlorophenyl isocyanate (7.65 g, 50 mmoles), N-(2-chloroethyl)-2-oxazolidinone (7.5 g, 50 mmoles) and anhydrous $AlCl_3$ (40 mg, 0.3 mmole) is heated at 195° C. for 6 hours with stirring. The reaction mixture is dissolved in dichloromethane and the resulting solution is washed with water twice. The dichloromethane solution is dried and evaporated and the residue distilled at reduced pressure. The distillate is recrystallized from hot hexane to give 10.2 g (78.4 percent) of the desired product, m.p. 64° C.

EXAMPLE 2

Preparation of N-(cyclohexyl)-N'-(2-chloroethyl)imidazolidinone

A mixture of cyclohexyl isocyanate (50 mmoles), N-(2-chloroethyl)-2-oxazolidinone (50 mmoles) and anhydrous $AlCl_3$ (40 mg, 0.3 mmole) is heated at 195° C. for 6 hours with stirring. The reaction mixture is dissolved in dichloromethane and the resulting solution is washed with water twice. The dichloromethane solution is dried and evaporated and the residue distilled at reduced pressure. The distillate is recrystallized from hot hexane to give a 50 percent yield of the desired product, m.p. 60° C.-64° C.

EXAMPLE 3

Preparation of N-phenyl-imidazolidinone

A mixture of phenyl isocyanate (50 mmoles), 2-oxazolidinone (50 mmoles) and anhydrous $AlCl_3$ (40 mg, 0.3 mmole) is heated at 195° C. for 6 hours with stirring. The reaction mixture is dissolved in dichloromethane and the resulting solution is washed with water twice. The dichloromethane solution is dried and evaporated and the residue distilled at reduced pressure. The distillate is recrystallized from hot hexane to give a yield of 48 percent of the desired product, m.p. 157° C.-159° C.

EXAMPLE 4

Preparation of N-(3-methylphenyl)-imidazolidinone

A mixture of 3-methylphenyl isocyanate (50 mmoles), 2-oxazolidinone (50 mmoles) and anhydrous $AlCl_3$ (40 mg, 0.3 mmole) is heated at 195° C. for 6 hours with stirring. The reaction mixture is dissolved in dichloromethane and the resulting solution is washed with water twice. The dichloromethane solution is dried and evaporated and the residue distilled at reduced pressure. The distillate is recrystallized from hot hexane to give a yield of 62 percent of the desired product, m.p. 137° C.-138° C.

EXAMPLE 5

Preparation of N-(3-nitrophenyl)-imidazolidinone

A mixture of 3-nitrophenyl isocyanate (50 mmoles), 2-oxazolidinone (50 mmoles) and anhydrous $AlCl_3$ (40 mg, 0.3 mmole) is heated at 195° C. for 6 hours with stirring. The reaction mixture is dissolved in dichloromethane and the resulting solution is washed with water twice. The dichloromethane solution is dried and evaporated and the residue distilled at reduced pressure. The distillate is recrystallized from hot hexane to give a yield of 33 percent of the desired product, m.p. 158° C-160° C.

EXAMPLE 6

Preparation of N-(3-chlorophenyl-imidazolidinone

A mixture of 3-chlorophenyl isocyanate (50 mmoles), 2-oxazolidinone (50 mmoles) and anhydrous $AlCl_3$ (40 mg, 0.3 mmole) is heated at 195° C. for 6 hours with stirring. The reaction mixture is dissolved in dichloromethane and the resulting solution is washed with water twice. The dichloromethane solution is dried and evaporated and the residue distilled at reduced pressure. The distillate is recrystallized from hot hexane to give a yield of 74 percent of the desired product, m.p. 121° C.-123° C.

EXAMPLE 7

Preparation of N-(3-chlorophenyl)imidazolidinone

A mixture of 2-oxazolidinone (4.41 g, 50 mmoles), N-(3-chlorophenyl)methyl carbamate (9.31 g, 50 mmoles) and anhydrous $AlCl_3$ (0.08 g) is heated at 200° C. with stirring for 6 hours. The mixture is distilled at reduced pressure and the distillate recrystallized from chloroform-hexane to give a yield of 54 percent of the desired product, m.p. 120° C.-123° C.

EXAMPLE 8

Preparation of N-phenylimidazolidinone

Following the procedure of Example 7, N-phenylmethyl carbamate is reacted with 2-oxazolidinone to give a yield of 55 percent of N-phenylimidazolidinone, m.p. 157° C.-159° C.

EXAMPLE 9

A series of experiments using various catalysts were completed using these conditions: 10 mmoles of N-(3-chlorophenyl)methyl carbamate, 10 mmoles of 2- oxazolidinones and 10 mg of catalyst heated at 200° C. for 5 hours. The reaction product was then analyzed by high pressure liquid chromatography using a $C_{18}$ reverse phase column and 1:1 water-acetonitrile as eluent. The results are given in the following table.

TABLE

| Catalyst | Yield (%) |
|---|---|
| $AlCl_3$ | 59 |
| $ZnCl_2$ | 58 |
| $NiCl_2$ | 54 |
| $NiCl_2.6H_2O$ | 47 |
| $FeCl_3$ | 45 |
| None* | 33 |

*Not an example of the invention.

What is claimed is:

1. A process for the preparation of N-substituted imidazolidinones and N-substituted 2-thionimidazolidinones which comprises contacting an oxazolidinone with a compound containing a nitrogen directly bonded to a carbonyl or a thiocarbonyl group in the presence of a Lewis acid catalyst or the hydrate of a Lewis acid catalyst under conditions such that an N-substituted imidazolidinone or N-substituted 2-thionimidazolidinone is prepared, wherein the compound containing a nitrogen directly bonded to a carbonyl or a thiocarbonyl group is an isocyanate or isothiocyanate or a compound wherein the nitrogen is reactive and the carbonyl or thiocarbonyl group is further bonded to a substituent by a bond which is cleavable under the reaction conditions, and the Lewis acid catalyst corresponds to the formula $$MX_n$$

wherein

M is a group IB-VIIIB, IIIA or IVA element with the proviso that M is not C or Si;

X is a halogen; and n is 2, 3 or 4.

2. The process of claim 1 wherein the compound with the nitrogen directly bonded to the carbonyl group is an isocyanate or isothiocyanate corresponding to the formula $$R^1N=C=Y$$

or a compound corresponding to the formula

wherein the oxazolidinone corresponds to the formula

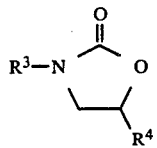

and the N-substituted imidazolidinone or N-substituted 2-thionimidazolidinone corresponds to the formula

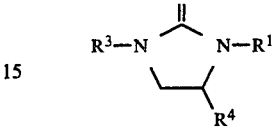

wherein $R^1$ is a $C_{1-20}$ hydrocarbyl radical optionally substituted with a halogen, aryloxy, alkoxy, nitro, thioaryloxy or thioalkoxy group;

$R^2$ is halogen, alkoxy, aryloxy, thioalkyl, thioaryl, mercapto, alkylsulfonamido, alkylsulfinyl, alkylsulfonoyl, alkylamino, arylamino, alkanoylamino or alkanoylimino;

$R^3$ is hydrogen or a $C_{1-20}$ hydrocarbyl radical optionally substituted with a halogen, aryloxy, alkoxy, aryl or nitro group;

$R^4$ is hydrogen or $R^3$; and

Y is oxygen or sulfur.

3. The process of claim 2 wherein $R^1$ is a $C_{6-20}$ aromatic or a $C_{6-20}$ cycloaliphatic radical optionally substituted with a $C_{1-10}$ alkyl, a $C_{6-10}$ aryl, halogen, nitro, aryloxy or alkoxy group; $R^2$ is a halogen, alkylamino, aryloxy or alkoxy group; $R^3$ is a $C_{1-20}$ alkyl group optionally substituted with a halogen; and $R^4$ is hydrogen.

4. The process of claim 3 wherein $R^1$ is a phenyl group optionally substituted with a $C_{1-10}$ alkyl group, halogen, nitro, aryloxy or alkoxy group.

5. The process of claim 4 wherein $R^1$ is a phenyl group optionally substituted with a methyl, nitro or chloro, and $R^3$ is hydrogen or β-chloroethyl.

6. The process of claim 1 wherein the nitrogen carbonyl compound is an isocyanate or isothiocyanate.

7. The process of claim 6 wherein the nitrogen carbonyl compound is an isocyanate.

8. The process of claim 1 wherein M is aluminum, zinc, nickel or iron.

9. The process of claim 1 wherein X is chlorine.

10. The process of claim 1 wherein the catalyst is aluminum chloride, zinc chloride, nickel chloride or iron chloride.

11. The process of claim 10 wherein the catalyst is aluminum chloride.

12. The process of claim 1 wherein the catalyst amount is between about 0.01 to 5.0 percent by weight of the compound containing a nitrogen directly bonded to a carbonyl or thiocarbonyl group.

13. The process of claim 12 wherein the catalyst amount is between about 0.1 and 2.0 percent based upon the weight of the compound containing a nitrogen bonded to a carbonyl or thiocarbonyl group.

14. The process of claim 1 wherein the reaction temperature is between about 150° C. to about 220° C.

15. The process of claim 1 wherein the reaction temperature is between 180° C. and 200° C.

16. The process of claim 2 wherein Y is oxygen..

* * * * *